US006994800B1

(12) United States Patent
Gordon et al.

(10) Patent No.: US 6,994,800 B1
(45) Date of Patent: Feb. 7, 2006

(54) LIQUID PRECURSORS FOR FORMATION OF MATERIALS CONTAINING ALKALI METALS

(75) Inventors: Roy G. Gordon, Cambridge, MA (US); Randy N. R. Broomhall-Dillard, Sunnyvale, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/019,458

(22) PCT Filed: Apr. 28, 2000

(86) PCT No.: PCT/US00/11415

§ 371 (c)(1),
(2), (4) Date: Jul. 12, 2002

(87) PCT Pub. No.: WO00/67300

PCT Pub. Date: Nov. 9, 2000

Related U.S. Application Data

(60) Provisional application No. 60/131,527, filed on Apr. 29, 1999.

(51) Int. Cl.
*C09K 3/00* (2006.01)
*C23C 16/06* (2006.01)
*H01L 21/00* (2006.01)
*B05D 3/01* (2006.01)
*B05D 3/12* (2006.01)

(52) U.S. Cl. .............................. 252/182.12; 252/182.3; 252/182.34; 252/183.11; 427/453; 427/455; 427/452; 427/226; 427/99; 427/126.1; 260/665 R

(58) Field of Classification Search ................ 427/453, 427/455, 226, 452, 99, 126.1; 252/183.11, 252/183.13; 260/665 R
See application file for complete search history.

(56) References Cited

U.S. PATENT DOCUMENTS

| 5,145,855 A | * | 9/1992 | Kosley et al. ............... 514/269 |
| 5,376,405 A | | 12/1994 | Doan et al. |
| 5,412,129 A | | 5/1995 | DiCarolis |
| 5,492,725 A | * | 2/1996 | Gordon ................... 427/248.1 |
| 5,581,396 A | | 12/1996 | Kubota et al. |
| 5,726,294 A | | 3/1998 | Rees, Jr. |
| 5,980,983 A | * | 11/1999 | Gordon ....................... 427/226 |
| 6,071,561 A | * | 6/2000 | Gordon et al. ............ 427/255.33 |
| 6,180,190 B1 | * | 1/2001 | Gordon ....................... 427/565 |
| 6,258,157 B1 | * | 7/2001 | Gordon ................... 106/287.24 |
| 6,806,004 B1 | * | 10/2004 | Iwamoto et al. ............ 429/313 |

OTHER PUBLICATIONS

Chemical Abstracts Accession No. 1986:571530 HCA-PLUS; "Dehydrohalogenation reaction using hindered lithium dialkylamide bases", By Kopka et al., Dep. Chem, Michigan State Univ. USA (1986).*

Chemical Abstracts Accession No. 2000:790762, "Liquid precursors for CVD formation of alkli metal compounds such as oxides", Gordon et al. Presendent and Fellows of Harvard College, USA (2000).*

Database Registry on STN: Derwent Publication Ltd., Accession No. 113:78097, Taken from J. Heterocycl. Chem. (1989), 26(6), pp. 1771-1780.

Database Registry on STN, Derwent Publication Ltd., Accession No. 107:96786, Taken from Chimia (1986), 40(6), pp. 202-205.

Chikuma et al. "Waveguiding Epitaxial Potassium Lithium Niobate Single-Crystal Films Deposited by Metalorganic Chemical Vapor Deposition." Jpn. J. Appl. Phys. vol. 37 (1998). pp. 5582-5587.

Feigelson. "Epitaxial Growth of Lithium Nobate Thin Films by the Solid Source MOCVD Method." J. Crystal Growth 166 (1996), pp. 1-16.

Tanaka et al. "Preparation of Lithium Niobate Films by Metalorganic Chemical Vapor Deposition with a Lithium Alkoxide Source." J. Crystal Growth 148 (1995), pp. 324-326.

Lingg et al. "Sodium Fluoride Thin Films by Chemical Vapor Deposition." Thin Solid Films, 209 (1992), pp. 9-16.

Chupp et al., Derivation of Fluorine-Containing Pyridinedicarboxylates. III Regio-selective Anion Chemistry at the 2- and 4-Position [1], J. Heterocyclic Chem, 26, 1771 (1989).

Niecke, et al., Synthese and Selbstadditionsverhalten von Iminophosphanen des Typs C-P=N-C(Si), Chimia, 40 (1986) Nr. 6, 202-205.

* cited by examiner

*Primary Examiner*—Joseph D. Anthony
(74) *Attorney, Agent, or Firm*—Wilmer Cutler Pickering Hale and Dorr LLP

(57) ABSTRACT

Volatile liquid precursors are provided for use in the formation of alkali metal-containing materials. The compound includes an alkali metal and an amide ligand and is a liquid at a temperature of less than about 70° C.

13 Claims, No Drawings

LIQUID PRECURSORS FOR FORMATION OF MATERIALS CONTAINING ALKALI METALS

This application claims the benefit of U.S. application Ser. No. 60/131,527, filed Apr. 29, 1999.

BACKGROUND OF THE INVENTION

1. Field of the Invention

This invention relates to novel volatile liquid reagents which can replace less satisfactory solid sources in film deposition processes such as chemical vapor deposition (CVD), spray coating, spin coating or sol-gel deposition. These liquid reagents can be used for deposition of materials containing alkali metals, such as metal oxides or mixed metal oxides.

2. Description of the Related Art

Chemical vapor deposition (CVD) is a widely-used process for forming solid materials, such as coatings or powders, from reactants in the vapor phase. Comprehensive reviews of CVD processes have been given recently in "CVD of Nonmetals," W. S. Rees, Jr., Editor, VCH Publishers, Weinheim, Germany, 1996; "CVD of Compound Semiconductors," A. C. Jones and P. O'Brien, VCH, 1996; and "The Chemistry of Metal CVD," T. Kodas and M. Hampden-Smith, Editors, VCH, 1994.

In CVD processes, a reactant vapor may be created by heating a liquid to a sufficiently high temperature and bubbling a flow of a carrier gas through the liquid, to transport the vapor into the CVD chamber. In a low-pressure CVD system, the carrier gas may be omitted, and the vapor may flow directly from the bubbler into the low-pressure CVD chamber.

In order for a CVD process to function successfully, it is necessary to create a vapor containing controlled amounts of suitably reactive chemicals. Solids can be used as sources of vapor in CVD processes. However, when solids are used in a bubbler, the rate of vapor production by sublimation of a solid is not easily reproducible, because the amount of vapor produced often depends on the particle size and shape, which change as the sublimation process continues. Thus the vapor concentration can change in an uncontrolled way, thereby changing the growth rate and/or the composition of materials made by the CVD process. Also, different batches of solid may have different sizes and shapes of particles, so that the results of a CVD process may change when a new batch of solid precursor is placed in the system. These difficulties are particularly evident in the currently-used solid CVD precursors, lithium 2,2,6,6-tetramethylheptane-3,5-dionate, often abbreviated Li(thd) or Li(dpm) and potassium 2,2,6,6-tetramethylheptane-3,5-dionate, K(thd), used by C. Kiyofumi, A. Onoe and A. Yoshida, Jpn. J. Appl. Phys., Part 1, vol. 37, pp. 5582–5587 (1998) and R. S. Feigelson, J. Cryst. Growth, vol. 166, pp. 1–16 (1996). Solid lithium tert-butoxide, LiO$^t$Bu, was used in the CVD of lithium niobate by A. Tanaka, K. Miyashita, T. Tashiro, M. Masakazu and T. Sukegawa, J. Cryst. Growth, vol. 148, pp. 324–326 (1995). Solid sodium hexfluoroisopropoxide was sublimed to provide vapors for CVD of sodium fluoride by L. J. Lingg, A. D. Berry, A. P. Purdy and K. J. Ewing, Thin Solid Films, vol. 209, pp. 9–16 (1992). None of these prior art sources for CVD of alkali metals are liquids at room temperature.

Another problem with solids is that their rate of sublimation can be altered by small amounts of contamination on their surfaces. In contrast, liquid surfaces tend to be refreshed by motion of the liquid, so that they tend to evaporate at a reproducible rate even in the presence of small amounts of contaminants.

Some solid materials show different vapor pressures, depending on the history of how the particular sample was prepared or how long it has been stored. For example, barium 2,2,6,6-tetramethylheptane-3,5-dionate, Ba(thd)$_2$, has been used to deposit barium strontium titanate (BST) films. Solid Ba(thd)$_2$ exists in a number of oligomeric forms, ranging from trimers to tetramers to polymers of various lengths, depending on the method used for its synthesis. The rates of interconversion between oligomeric forms are slow, often taking weeks or months. Thus the molecular composition of a sample of Ba(thd)$_2$ depends on how it was made and how long it has been stored. The vapor pressures of these oligomers are different from each other. Thus it is very difficult to predict the vapor pressure of any particular sample of Ba(thd)$_2$ and the deposition rate of BST from this solid source is not reproducible. In comparison, liquids usually exist in only one reproducible form at any given temperature and pressure.

Another difficulty with solids is that rates of sublimation are often low, so that sufficiently high vapor concentrations cannot be produced. For example, K(thd) has a very low vapor pressure, which limits the deposition rate to low values. In comparison, liquids often have higher vapor pressures than solids. Another practical difficulty with solids is that transferring them between containers is less convenient than pumping liquids.

Thermal decomposition of solids is another problem that often affects the reproducibility of solid vapor sources. For example, solid K(thd) gradually decomposes at its sublimation temperature, so that the amount of vapor generated decreases with time. Thermal decomposition is also a potential problem for liquid sources, but its effect may be minimized for liquids by rapid or "flash" vaporization. This can be accomplished by pumping the liquid at a steady, controlled rate into a hot region in which the liquid vaporizes quickly. In such a "direct liquid injection" (DLI) system, each part of the liquid is heated for only a short time, and its vapor can be formed without significant decomposition even from thermally sensitive liquids. Another advantage of a DLI system is that multi-component mixtures can be vaporized in a fixed and reproducible ratio, even if the components differ in volatility. Because of these advantages, DLI systems are becoming more widely used in CVD processes.

Solid sources can be used in DLI vapor sources if a suitable liquid solvent can be found to dissolve the solid. However, solvents can introduce other difficulties, such as increased flammability, toxicity or corrosiveness of the precursor solution, increased incorporation of carbon or other impurities into the deposited film, and an increased volume of gaseous byproducts must be removed from the exhaust gases to avoid pollution.

Because of all these difficulties, solid sources of vapor are seldom used in commercial CVD processes. Sources that are liquid at room temperature are more convenient, and are almost always used in the practice of CVD where available. Creating a vapor from a liquid source would be much more reproducible and convenient than creating it from a solid source; however, there are no previously known volatile compounds of the alkali metals that are liquid at room temperature.

SUMMARY OF THE INVENTION

A principal feature of the present invention includes chemical precursors that are pure liquid compounds at room temperature, and that may be used for the deposition of materials containing alkali metals, particularly lithium, sodium and potassium.

An advantage of these chemical precursors is that they are easily vaporized without decomposition, and that they do not leave a nonvolatile residue during a process for the chemical vapor deposition of alkali metal-containing materials.

A related feature of the present invention is the deposition of alkali metal-containing materials from chemical compounds that are liquids at room temperature.

An advantage of the process is that it permits deposition of materials containing several metals by a chemical vapor deposition process in which all the reactants may be mixed homogeneously before delivery to the heated surface of the substrate.

An additional advantage of the deposition of alkali metal-containing materials from chemical precursors is that they are easily vaporized without decomposition, and that do not leave a nonvolatile residue.

Another feature of the present invention is the preparation of mixed metal oxides, including alkali metal oxides, having high purity.

An advantage of the process for preparing metal oxides is that the reactants are stable and relatively nonhazardous.

Another feature of the invention includes a chemical vapor or solution deposition process for complex metal oxides in which the precursor metal-containing compounds are stable and homogeneous liquids.

A further feature of the invention includes liquid mixtures or solutions suitable for spray coating, spin coating or sol-gel deposition.

One particular feature of the present invention includes a process for depositing lithium niobate coatings having non-linear optical properties.

Another particular feature of the present invention includes a process for depositing tungsten bronzes having useful optical and electrical properties.

An additional feature of the present invention includes a process for depositing lithium-containing materials for use as electrodes in batteries.

A further feature of the present invention includes a process for depositing alkali-doped electrochromic materials.

Other features and advantages of the invention will be obvious to those skilled in the art on reading the instant invention.

The above features and advantages have been substantially achieved by use of a composition comprising alkali metal alkylamides. The preferred compounds have the general formula

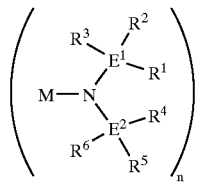

where M is an alkali metal; $E^1$ and $E^2$ may be the same or different and are tetravalent atoms selected from the group consisting of carbon, silicon, germanium or tin, and $R^1$, $R^2$, $R^3$, $R^4$, $R^5$ and $R^6$ may be the same or different represent and are selected from the group consisting of hydrogen, alkyl groups, fluoroalkyl groups or alkyl groups substituted by other atoms or groups, wherein at least one of $R_1$, $R^2$, $R^3$, $R^4$, $R^5$ and $R_6$ contains more than one carbon atom, and wherein one or more carbons may be replaced by an isoelectronic species, and n is a number equal to or greater than one. The number n represents the degree of association of the molecules. Typical values of n were found to lie between two and three, corresponding to dimers and trimers. It is believed that these oligomers are attached together by bonds in which nitrogen atoms form bridges between metal atoms.

Preferred compounds include the alkali metal bis(alkyldimethylsilyl)amides represented by the general formula

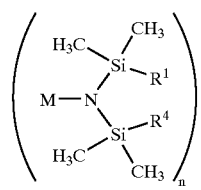

in which M is an alkali metal and $R^1$ and $R^4$ represent alkyl groups which may be the same or different and n is in the range of 1 to 3. In the most preferred embodiments, the alkyl groups contain between two and eight carbons.

A typical preferred compound of this class may be represented by the formula

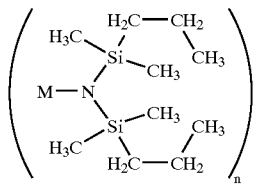

in which M is lithium, sodium or potassium, and $R^1$ and $R^4$ are n-propyl groups and n is in the range of 1 to 3, and is preferably in the range of 2 to 3.

In the most preferred embodiments, the alkali metal amide is a liquid at 70° C., and more preferably at room temperature, e.g., 20° C. It is believed that the long alkyl chains on the amine ligand promote the formation of the liquid phase by interfering with the formation of a regular crystal structure.

Another aspect of the invention provides a process for the chemical vapor deposition of materials comprising alkali metals, using vapors from a liquid alkali metal amide and, optionally, another oxygen-containing gas such as air. The process may be used to form metal oxide films, including, but not limited to, oxides of lithium, sodium and potassium. A preferred embodiment uses a homogeneous vapor mixture comprising an alkali metal amide, oxygen and, optionally, an inert carrier gas such as nitrogen. This vapor mixture is brought into contact with a substrate heated to a temperature sufficient to deposit a material comprising one or more alkali metals. Typical deposition temperatures lie in the range of about 200 to 800° C. Typical deposition pressures range from normal atmospheric pressure down to a few milli-Torr.

Another preferred embodiment uses a homogeneous liquid mixture of one or more alkali metal amides along with one or more other volatile metal-containing compounds. This liquid mixture is vaporized to form a vapor mixture and, optionally mixed with an oxygen-containing gas, such as air, and an inert carrier gas such as nitrogen. This vapor mixture is heated to a temperature sufficient to cause reaction and the formation of a material comprising two or more metal oxides. Alternatively, the energy required to initiate the reaction may be provided by light, or by the electrical energy of a plasma discharge. The process may be used to form multimetal oxide films, including, but not limited to, lithium niobate, potassium tantalate and sodium tungsten bronze.

In another embodiment of the invention, multimetal oxides are formed from solutions of one or more alkali metal amides along with one or more other volatile metal-containing compounds and a solvent, in deposition processes as described herein.

DETAILED DESCRIPTION OF THE INVENTION

1. Amine Ligands. Table 1 identifies a non-limiting list of amine ligands that are suitable for the practice of the invention. The general formula for the amine ligands may be written as:

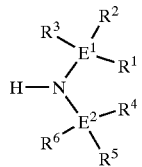

in which $E^1$ or $E^2$ may be any tetravalent atom, including carbon, silicon, germanium or tin.

TABLE 1

Exemplary amine ligands

| Name[a] | $E^1$ | $E^2$ | $R^1$ | $R^4$ | t |
|---|---|---|---|---|---|
| bis(n-octyldimethylsilyl)amine | Si | Si | n-Oct | n-Oct | 14 |
| bis(n-hexyldimethylsilyl)amine | Si | Si | n-Hex | n-Hex | 10 |
| bis(n-butyldimethylsilyl)amine | Si | Si | n-Bu | n-Bu | 6 |
| bis(isobutyldimethylsilyl)amine | Si | Si | i-Bu | i-Bu | 4 |
| bis(n-propyldimethylsilyl)amine | Si | Si | n-Pr | n-Pr | 4 |
| tert-amyl(n-butyldimethylsilyl)amine | C | Si | Et | n-Bu | 4 |
| tert-amyl(i-butyldimethylsilyl)amine | C | Si | Et | i-Bu | 3 |
| tert-amyl(n-propyldimethylsilyl)amine | C | Si | Et | n-Pr | 3 |
| tert-butyl(n-butyldimethylsilyl)amine | C | Si | Me | n-Bu | 3 |
| tert-amyl(isopropyldimethylsilyl)amine | C | Si | Et | i-Pr | 2 |
| bis(ethyldimethylsilyl)amine | Si | Si | Et | Et | 2 |
| bis(tert-butyldimethylsilyl)amine | Si | Si | t-Bu | t-Bu | 2 |
| tert-amyl(ethyldimethylsilyl)amine | C | Si | Et | Et | 2 |
| tert-butyl(n-propyldimethylsilyl)amine | C | Si | Me | n-Pr | 2 |
| tert-amyl(trimethylsilyl)amine | C | Si | Et | Me | 1 |
| tert-butyl(ethyldimethylsilyl)amine | C | Si | Me | Et | 1 |
| tert-amyl-tert-butylamine | C | C | Et | Me | 1 |

[a]$R^2 = R^3 = R^5 = R^6 = $ methyl

The number t in this table is the number of angular variables (torsion angles corresponding to rotation around C—C single bonds) in excess of those present in the reference compound bis(trimethylsilyl)amine which is a solid at room temperature. Methyl rotations about their three-fold axes were not counted, since these motions don't change the intermolecular interactions as much as the other torsions do. As t increases, the number configurations available to the ligand increases, and thus its ability to impede crystallization. Thus the larger t is, the greater is the ability of the ligand to keep the corresponding metal-ligand compounds in liquid form at room temperature. For the purposes herein, room temperature shall mean about 20° C.

Some or all of the carbons in the amine ligands may be replaced by isoelectronic species, such as silicon or germanium. For the purposes of this specification and claims, these isoelectronically substituted amine ligands shall be considered as amine ligands.

Some or all of the hydrogens in the amide ligands may be replaced by fluorine. Fluorine substitution may be used to deposit fluorides instead of oxides. Fluorine substitution may also provide higher vapor pressures of the precursor compounds.

2. Synthesis of Bis(Trialkylsilyl)Amide Ligands. The preferred bis(trialkylsilyl)amines may be prepared by known methods, such as the condensation of ammonia with a trialkylchlorosilane. A detailed description of

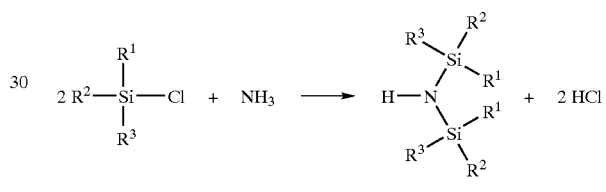

this procedure is given in Inorganic Syntheses, vol. 5, pp. 55–64 (1957). Distillation under low pressure then yields the desired bis(trialkylsilyl)amine.

3. Synthesis of Alkyl(Trialkylsilyl)Amide Ligands. Alkyl (trialkylsilyl)amines may be synthesized by condensation of primary amines with trialkylchlorosilanes, according to the general reaction:

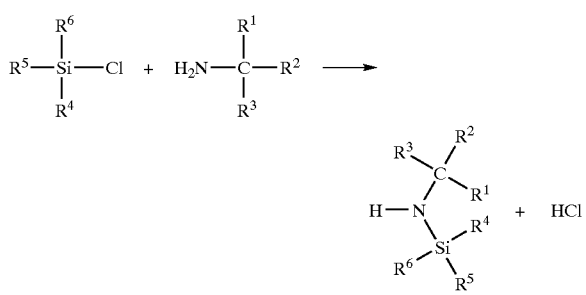

For example, n-butyldimethylchlorosilane reacts with tert-amylamine (commercially available from Aldrich) to form tert-amyl(n-butyldimethylsilyl)amine.

To obtain some tertiary amines that are not commercially available, one may convert the corresponding neo-acid chlorides (commercially available from PPG Industries) into amines using the Curtius rearrangement:

$R'COCl + NaN_3 \rightarrow R'CON_3 + NaCl$ $R'CON_3 + H_2O \rightarrow R'NH_2 + CO_2 + N_2$ 4. Synthesis of Alkali Amides. Compounds can be formed between these amide ligands and the alkali metals in various ways. For lithium, it is convenient to react a solution of butyl lithium with the amine:

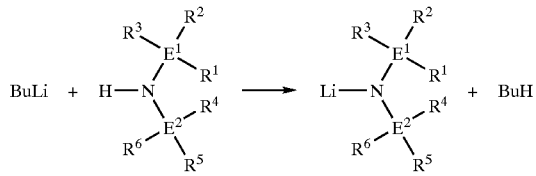

Sodium amide may be reacted with amine ligands to form liquid sodium compounds:

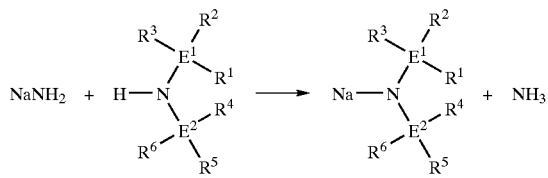

Potassium precursors may be prepared by the transamination reaction of potassium bis(trimethylsilyl)amide with the amine ligands:

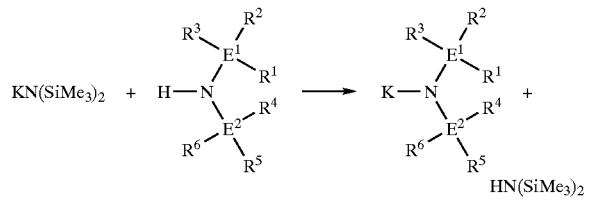

5. Use of Alkali Metal Amides. The novel alkali metal amides of this invention are generally liquids at room temperature. The vapor of these liquids may be formed in a thin-film evaporator, or by nebulization into a carrier gas preheated to about 150 to 250° C. The nebulization may be carried out pneumatically or ultrasonically. The liquid alkali metal amides are generally completely miscible with organic solvents, including hydrocarbons, such as dodecane, tetradecane, xylene and mesitylene, and with ethers, esters, ketones and chlorinated hydrocarbons. These solutions generally have lower viscosities than the pure liquids, so that in some cases it may be preferable to nebulize and evaporate the solutions rather than the pure liquids. In these instances, however, very concentrated solutions, e.g. greater than one molar, may be obtained. The liquids or solutions can also be evaporated with thin-film evaporators or by direct injection of the liquids into a heated zone. Thin-film evaporators are made by Artisan Industries (Waltham, Mass.). Commercial equipment for direct vaporization of liquids is made by MKS Instruments (Andover, Mass.), Advanced Technology Materials Inc. (Danbury, Conn.), Novellus Systems, Inc. (San Jose, Calif.) and COVA Technologies (Tiburton, Calif.). Ultrasonic nebulizers are made by Sonotek Corporation (Milton, N.Y.) and Cetac Technologies (Omaha, Nebr.).

The process of the invention can be carried out in standard equipment well known in the art of chemical vapor deposition (CVD). The CVD apparatus brings the vapors of the reactants into contact with a heated substrate on which the material deposits. A CVD process can operate at a variety of pressures, including in particular normal atmospheric pressure, and also lower pressures. Commercial atmospheric pressure CVD furnaces are made in the USA by the Watkins-Johnson Company (Scotts Valley, Calif.), BTU International (North Billerica, Mass.) and SierraTherm (Watsonville, Calif.). Commercial atmospheric pressure CVD equipment for coating glass on the float production line is made in the USA by Pilkington-Libbey-Owens-Ford Company (Toledo, Ohio), PPG Industries (Pittsburgh, Pa.) and AFG Industries (Kingsport, Tenn.). Low-pressure CVD equipment is made by Applied Materials (Santa Clara, Calif.), Spire Corporation (Bedford, Mass.), Materials Research Corporation (Gilbert, Ariz.), Novellus Systems, Inc. (San Jose, Calif.), Emcore Corporation (Somerset, N.J.), NZ Applied Technologies (Woburn, Mass.) and CVC Corporation (Freemont, Calif.).

The liquid precursors of the present invention may be combined with niobium to provide a process for depositing lithium niobate films having nonlinear optical properties, as is shown in Example 22. Similarly, the liquid precursors of the present invention may be combined with tantalum precursors to provide a process for depositing potassium tantalate films having non-linear optical properties. Similarly, sodium-potassium niobate (NKN) films may be formed with low loss tangent and a strong electric field dependence of rather low dielectric permittivity, and used in tunable microwave devices. $Na_{0.1}K_{0.9}Ta_{0.55}Nb_{0.45}O_3$ films with high pyroelectric sensitivity may be made by methods of the invention and fabricated into night-vision devices. By using a tungsten-containing precursor along with precursors made according to this invention, tungsten bronzes having useful optical, electrical and electrochromic properties may be made and formed into electrochromic windows, mirrors and displays. Similarly, by combining liquid lithium precursors of this invention with precursors for cobalt, nickel and/or other transition metals, electrochromic materials or electrodes for lithium batteries may be deposited. Vapors of a sodium-containing precursor can be used to supply sodium dopant for copper indium diselenide solar cells.

The liquids and solutions described herein may also be used as metal-containing precursors for other types of deposition processes, such as spray coating, spin coating or sol-gel formation of mixed metal oxides. The high solubility and miscibility of these precursors is an advantage in forming the required solutions.

The liquids and solutions disclosed in these examples all appeared to be non-pyrophoric by the methods published by the United States Department of Transportation. One test calls for placing about 5 milliliters of the liquid or solution on an non-flammable porous solid, and observing that no spontaneous combustion occurs. Another test involves dropping 0.5 milliliters of the liquid or solution on a Whatman No. 3 filter paper, and observing that no flame or charring of the paper occurs.

The precursors generally react with moisture in the ambient air, and should be stored under an inert, dry atmosphere such as pure nitrogen gas.

The invention may be understood with reference to the following examples which are for the purpose of illustration only and which are not limiting of the invention, the full scope of which is set forth in the claims which follow.

EXAMPLE 1

As a specific example of this method, the synthesis of bis(ethyldimethylsilyl)amine is given as follows: All experimental manipulations were carried out using standard Schlenk techniques under dry nitrogen either in a glove box or on a Schlenk line unless otherwise stated. Commercial (Gelest, Inc. or United Chemical Technologies) ethyldimethylchlorosilane (100 g, 0.82 mmol) was dissolved in 400 mL of dry ether. Ammonia gas was bubbled into the solution until it was no longer absorbed, and then for an additional hour in order to be sure that the reaction was complete. The solution was refluxed for one hour and the solid byproduct $NH_4Cl$ was removed by filtration. Distillation was used to remove the ether and excess ammonia, yielding a colorless liquid (65.9 g, 85%) which was shown to be the desired product, bis(ethyldimethylsilyl)amine, by NMR analysis. $^1H$ NMR (in $C_6D_6$) showed shifts, in ppm, of 0.96 (t, 3H), 0.50 (q, 2H), 0.06 (s, 6H). $^{13}C$ NMR (in $C_6D_6$) showed shifts, in ppm, of 11.2, 7.77, 0.60.

Other bis(trialkylsilyl)amines were made in a similar manner, by substituting other trialkylchlorosilanes for ethyldimethylchlorosilane.

EXAMPLE 2

Lithium bis(ethyldimethylsilyl)amide was prepared by the slow addition via syringe of a hexane solution of butyl lithium (50.6 mL of 2.73 M solution, 138 mmol) to a stirred hexane solution (100 mL) of bis(ethyldimethylsilyl)amine (26.2 g, 138 mmol) at room temperature. Stirring was continued for one hour and the solution was then refluxed for one hour. The hexane was evaporated under vacuum, leaving a pale yellow liquid. It was distilled at a temperature of 123° C. and a pressure of 0.2 torr to yield 23.2 g (86%) of clear liquid lithium bis(ethyldimethylsilyl)amide. Its viscosity was measured to be 37.5 centipoise at 40° C. Its NMR parameters are as follows:

$^1HNMR$ ($C_6D_6$) shifts 0.99 (t, 3H), 0.54 (q, 2H), 0.09 (s, 6H). $^{13}C$ NMR ($C_6D_6$) shifts 13.3, 8.55, 2.50.

EXAMPLES 3–12

Similar methods were used to prepare other distillable liquid lithium compounds having the properties listed in Table 2.

TABLE 2

Liquid lithium amides

| No. | Lithium salt | $E^1$ | $E^2$ | $R^1$ | $R^4$ | Viscosity (centipoise @ 40° C.) | Vapor Pressure (° C./Torr) |
|---|---|---|---|---|---|---|---|
| 1 | bis(ethyldimethylsilyl)amide | Si | Si | Et | Et | 37.5 | 123/0.2 |
| 2 | bis(n-propyldimethylsilyl)amide | Si | Si | n-Pr | n-Pr | 23.3 | 130/0.15 |
| 3 | bis(n-butyldimethylsilyl)amide | Si | Si | n-Bu | n-Bu | 22.4 | 145/0.085 |
| 4 | bis(i-butyldimethylsilyl)amide | Si | Si | i-Bu | i-Bu | 32.9 | 145/0.05 |
| 5 | bis(3,3-dimethylbutyldimethylsilyl)amide | Si | Si | $Z^1$ | $Z^1$ | 247 | 225/0.9 |
| 6 | bis(n-hexyldimethylsilyl)amide | Si | Si | n-Hex | n-Hex | 26 | |
| 7 | bis(n-octyldimethylsilyl)amide | Si | Si | n-Oct | n-Oct | 45 | |
| 8 | tert-amyl(triethylsilyl)amide | C | Si | Et | $Z^2$ | 162 | 157/0.095 |
| 9 | tert-amyl(n-butyldimethylsilyl)amide | C | Si | Et | n-Bu | 368 | 158/0.2 |
| 10 | tert-amyl(i-butyldimethylsilyl)amide | C | Si | Et | i-Bu | 497 | 145/0.1 |
| 11 | tert-amyl(n-propyldimethylsilyl)amide | C | Si | Et | n-Pr | 810 | 171/0.3 |
| 12 | tert-amyl(i-propyldimethylsilyl)amide | C | Si | Et | i-Pr | 409 | 137/0.2 |

$Z^1 = (CH_2)_2C(CH_3)_3$; $Z^2 = R^4, R^5, R^6 = Et$

Tert-amyl(n-butyldimethylsilyl)amide, Example 9, existed as a supercooled liquid at room temperature. After standing at room temperature for several days, some samples of tert-amyl(n-butyldimethylsilyl)amide solidified.

EXAMPLE 13

Sodium bis(n-propyldimethylsilyl)amide was prepared as follows: Sodium amide (1.26 g, 0.0322 mol) was placed in dry benzene and bis(n-propyldimethylsilyl)amine (7.00 g, 0.0322 mol) was added. The mixture was stirred and refluxed for several hours. The benzene solution was filtered through celite and then the benzene was evaporated under vacuum, leaving 6.31 g (82%) of a yellow liquid product, sodium bis(n-propyldimethylsilyl)amide. Its viscosity was measured to be $7.1 \times 10^4$ centipoise at 40° C. It was distilled at a temperature of 213° C. and a pressure of 0.3 torr.

EXAMPLES 14–16

Similar methods were used to prepare other distillable liquid sodium compounds having the properties listed in Table 3.

TABLE 3

Liquid sodium amides

| No. | Sodium salt | E$^1$ | E$^2$ | R$^1$ | R$^4$ | Viscosity (centipoise @ 40° C.) | Vapor Pressure (° C./Torr) |
|---|---|---|---|---|---|---|---|
| 13 | bis(n-propyldimethylsilyl)amide | Si | Si | n-Pr | n-Pr | 7.1 × 10$^4$ | 213/0.3 |
| 14 | bis(n-butyldimethylsilyl)amide | Si | Si | n-Bu | n-Bu | >10$^7$ | 231/0.5 |
| 15 | bis(i-butyldimethylsilyl)amide | Si | Si | i-Bu | i-Bu | 2.8 × 10$^4$ | 189/0.08 |
| 16 | bis(n-hexyldimethylsilyl)amide | Si | Si | n-Hex | n-Hex | 1.5 × 10$^4$ | |

EXAMPLE 17

Potassium bis(n-hexyldimethylsilyl)amide was prepared as follows: Potassium bis(trimethylsilyl)amide (5.07 g, 25.6 mmol) and bis(n-hexyldimethylsilyl)amine (7.66 g, 25.6 mmol) were added to a flask and 50 mL toluene was added. The clear yellow solution was stirred at room temperature for 18 hours and then refluxed for two hours. The toluene and hexamethyldisilazane byproduct were removed from the brown toluene solution under vacuum with heating to 150° C. to yield a brown oil (5.40 g, 63%). Its viscosity was measured to be 271 centipoise at 40° C. It may be flash vaporized from a heated nozzle for CVD applications. Alternatively, it may be dissolved in small amounts of organic solvents to form concentrated solutions that may be flash vaporized.

EXAMPLES 18–21

Similar methods were used to prepare other vaporizable liquid potassium compounds having the properties listed in Table 4.

TABLE 4

Potassium precursors

| No. | Potassium salt | E$^1$ | E$^2$ | R$^1$ | R$^4$ | Viscosity (centipoise @ 40° C.) | Melting Point (° C.) |
|---|---|---|---|---|---|---|---|
| 17 | bis(n-hexyldimethylsilyl)amide | Si | Si | n-Hex | n-Hex | 271 | <20 |
| 18 | bis(n-octyldimethylsilyl)amide | Si | Si | n-Oct | n-Oct | 183 | <20 |
| 19 | bis(n-butyldimethylsilyl)amide | Si | Si | n-Bu | n-Bu | 230 | 45 |
| 20 | bis(i-butyldimethylsilyl)amide | Si | Si | i-Bu | i-Bu | 205 | 53 |
| 21 | bis(n-propyldimethylsilyl)amide | Si | Si | n-Pr | n-Pr | solid | 70 |

EXAMPLE 22

Liquid lithium bis(ethyldimethylsilyl)amide was mixed with mesitylene to lower the viscosity below 4 centipoise so that the precursor solution could be nebulized into tiny droplets (about 20 microns in diameter) by a high-frequency (1.4 MHz) ultrasonic system. The resulting fog was carried by a nitrogen and oxygen gas mixture into the deposition zone inside a glass tube (22 cm inside diameter) in a furnace heated to 200° C. The precursor concentration in the input gas stream was 0.36 mol %, the oxygen concentration was 17 mol %, and the total flow rate was 0.60 L/min. A thin film was deposited on a silicon substrate placed on the bottom of the glass tube, as well as on the inside of the tube. Flame tests showed that the film contains lithium. The lithium-containing film was easily dissolved in water. The refractive index of the film was determined to be 1.48–1.49, by using drops of Cargille certified index of refraction fluids. This value more closely resembles lithium hydroxide (1.45–1.46) than lithium oxide (1.64).

EXAMPLE 23

Films were produced containing both lithium and niobium by mixing liquid lithium bis(ethyldimethylsilyl)amide and liquid ethylimidotris(diethylamido)niobium(V) with mesitylene in a 1:1:5 mole ratio. Films were deposited from the mixed precursor by the same method used in Example 22, except that the substrate was heated to 250° C. The concentration of the lithium precursor in the input gas stream was 0.27 mol %, the niobium precursor concentration was 0.27 mol %, the oxygen concentration was 16 mol %, and the total flow rate was 0.60 L/min. The silicon substrates were coated with an iridescent film. The lithium to niobium ratio in the resulting film was determined by ablating the film with a 193 nm argon fluoride excimer laser and analyzing the ablated atoms by quadrupole mass spectrometry. An approximate Li:Nb ratio of 0.3:1 was observed for most of the film, indicating that the niobium was more efficiently deposited than lithium under these conditions. The silicon-containing lithium precursor did not deposit a detectable amount of silicon impurity in the film.

Those skilled in the art will recognize or be able to ascertain using no more than routine experimentation, many equivalents to the specific embodiments of the invention described specifically herein. Such equivalents are intended to be encompassed in the scope of the following claims.

What is claimed is:

1. A composition for use in the formation of alkali metal-containing materials, comprising:
  an alkali metal amide compound, said compound being a liquid at a temperature in the range of about 20° C. to about 70° C. and forming a vapor at a temperature of between about 150° C. and 250° C.

2. The composition as in claim 1, wherein the alkali metal amide has the formula

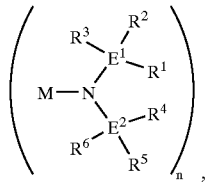

where M is an alkali metal; $E^1$ and $E^2$ may be the same or different and are tetravalent atoms selected from the group consisting of carbon, silicon, germanium or tin, and $R^1$, $R^2$, $R^3$, $R^4$, $R^5$ and $R^6$ may be the same or different and are selected from the group consisting of hydrogen, alkyl groups, fluoroalkyl groups or alkyl groups substituted by other atoms or groups, wherein at least one of $R^1$, $R^2$, $R^3$, $R^4$, $R^5$ and $R^6$ contains more than one carbon atom, and wherein one or more carbons may be replaced by an isoelectronic species, and n is in the range of 1 to 3.

3. The composition of claim 2, wherein the groups $R^1$ and $R^4$ contain between two and eight carbons and may be the same or different.

4. The composition of claim 3, wherein the groups $R^2$, $R^3$, $R^5$ and $R^6$ contain less than three carbons and may be the same or different.

5. The composition of claim 2, wherein the E1 and E2 are selected from the group consisting of carbon and silicon and may be the same or different.

6. The composition of claim 1, wherein the alkali metal is lithium.

7. The composition of claim 1, wherein the alkali metal is sodium.

8. The composition of claim 1, wherein the alkali metal is potassium.

9. The composition of claim 2, wherein n is in the range of 2 to 3.

10. The composition of claim 1, wherein the liquid has a viscosity at 40° C. in the range of about 200–1000 cP.

11. A composition for use in the formation of alkali metal-containing materials comprising a liquid alkali metal amide, said amide being a liquid at a temperature in the range of about 20° C. to about 70° C., and having the formula

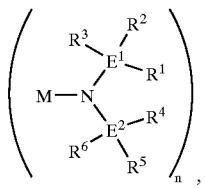

where M is an alkali metal; $E^1$ and $E^2$ may be the same or different and are tetravalent atoms selected from the group consisting of carbon, silicon, germanium or tin, and $R^1$, $R^2$, $R^3$, $R^4$, $R^5$ and $R^6$ may be the same or different and are selected from the group consisting of hydrogen, alkyl groups, fluoroalkyl groups or alkyl groups substituted by other atoms or groups, wherein at least one of $R^1$, $R^2$, $R^3$, $R^4$, $R^5$ and $R^6$ contains more than one carbon atom, and wherein one or more carbons may be replaced by an isoelectronic species, and n is in the range of 1 to 3, and wherein the number of angular variables of the amide in excess of those present in the reference bis(trimethylsilyl)amine is greater than six.

12. The composition of claim 11, wherein $E^1=E^2=Si$.

13. A composition for use in the formation of alkali metal-containing materials comprising a liquid alkali metal amide, said amide being a liquid at a temperature in the range of about 20° C. to about 70° C. and having the formula

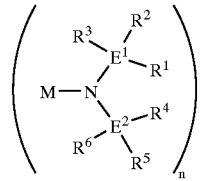

where M is an alkali metal; $E^1$ and $E^2$ may be the same or different and are tetravalent atoms selected from the group consisting of carbon, silicon, germanium or tin, and $R^1$, $R^2$, $R^3$, $R^4$, $R^5$ and $R^6$ may be the same or different and are selected from the group consisting of hydrogen, alkyl groups, fluoroalkyl groups or alkyl groups substituted by other atoms or groups, wherein at least one of $R^1$, $R^2$, $R^3$, $R^4$, $R^5$ and $R^6$ contains more than one carbon atom, and wherein one or more carbons may be replaced by an isoelectronic species, and n is in the range of 1 to 3, with the proviso that when $R^1$ and/or $R^4$ are tert-butyl, then at least one of $R^2$, $R^3$, $R^5$ and $R^6$ is not methyl, and when $R^1$ and $R^4$ are ethyl, then $R^2$, $R^3$, $R^5$ and $R^6$ are not methyl or ethyl.

* * * * *

UNITED STATES PATENT AND TRADEMARK OFFICE
CERTIFICATE OF CORRECTION

| | |
|---|---|
| PATENT NO. | : 6,994,800 B1 |
| APPLICATION NO. | : 10/019458 |
| DATED | : February 7, 2006 |
| INVENTOR(S) | : Roy G. Gordon et al. |

It is certified that error appears in the above-identified patent and that said Letters Patent is hereby corrected as shown below:

Column 1, below the title, insert
-- STATEMENT AS TO FEDERALLY SPONSORED RESEARCH
This invention was made with support from the National Science Foundation Grant No. NSF CHE-95-10245.
Accordingly, the U.S. government may have certain rights in the invention. --

Signed and Sealed this

Nineteenth Day of December, 2006

JON W. DUDAS
*Director of the United States Patent and Trademark Office*